United States Patent [19]

Steckler

[11] 4,036,788

[45] July 19, 1977

[54] ANIONIC HYDROGELS BASED ON HETEROCYCLIC N-VINYL MONOMERS

[75] Inventor: Robert Steckler, Del Mar, Calif.

[73] Assignee: Plastomedical Sciences, Inc., Briarcliff Manor, N.Y.

[21] Appl. No.: 549,095

[22] Filed: Feb. 11, 1975

[51] Int. Cl.$^2$ .................................... C08F 220/20
[52] U.S. Cl. ............................ 260/2.1 E; 71/27; 204/159.22; 260/79.3 MU; 424/224; 424/248.4; 424/256; 424/269; 424/274; 526/227; 526/240; 526/260; 526/263; 526/264
[58] Field of Search ............... 260/80.72, 79.3 MU, 260/2.1 E

[56] References Cited

U.S. PATENT DOCUMENTS

| | | | |
|---|---|---|---|
| 3,178,397 | 4/1965 | Olaj et al. | 260/80.72 |
| 3,493,500 | 2/1970 | Volk et al. | 260/80.72 |
| 3,532,679 | 10/1970 | Steckler | 260/80.72 |
| 3,692,893 | 9/1972 | Palmer | 260/80.72 |
| 3,721,657 | 3/1973 | Seiderman | 260/80.72 |
| 3,839,304 | 10/1974 | Hovey | 260/80.72 |

*Primary Examiner*—Harry Wong, Jr.
*Attorney, Agent, or Firm*—George L. Tone

[57] ABSTRACT

Novel anionic hydrogels, containing acidic groups, and their preparation are described. These novel hydrogels are stable, three-dimensional polymer networks, having good water permeability and mechanical properties. They are obtained by simultaneous polymerization and cross-linking, in the presence of a polymerization catalyst, such as an organic peroxide, azobisisobutyronitrile or other free radical polymerization catalyst, of a mixture of (a) a heterocyclic monomer preferably an N-vinyl lactam, (b) a polymerizable acidic monomer, such as acrylic or methacrylic acid, sulfo-ethyl methacrylate or a sulfated or phosphated derivative of a hydroxyalkyl- acrylate or methacrylate and (c) a cross-linking agent, such as a glycol or polyglycol diacrylate or dimethacrylate and also, preferably, (d) at least one acrylic monomer capable of polymerizing to a very high molecular weight, such as hydroxyethyl- or hydroxypropyl-acrylate or methacrylate, acrylamide or methacrylamide, or a lower alkyl acrylate or methacrylate; if desired there may also be present in the monomer mixture (e) other polymerizable ethylenically unsaturated monomers, which are copolymerizable with components (a), (b), (c) and (d). The thus obtained anionic hydrogels are useful for combining by reaction or complexing, with water soluble or dispersible materials having an opposite charge; such as basic or cationic agricultural chemicals (insecticides, herbicides, fungicides, plant growth regulators, etc.), germicides, pharmaceuticals, cosmetics, hormones, enzymes, flavors, fragrances, antiperspirants, metals and the like, both to recover such basic or cationic materials from an aqueous medium and for purifying water containing them, and also for the preparation of a complex or other combination of the anionic hydrogel with such materials which may be useful per se or from which the complexed or combined basic or cationic material may be slowly or controllably released.

10 Claims, No Drawings

ANIONIC HYDROGELS BASED ON HETEROCYCLIC N-VINYL MONOMERS

The present invention relates to new and useful anionic hydrogels which are stable three dimensional copolymer networks, having good water permeability and mechanical properties, and are obtained by simultaneous copolymerization and cross-linking, in the presence of a polymerization catalyst, of a mixture of (a) a heterocyclic N-vinyl monomer, preferably an N-vinyl lactam, (b) a polymerizable ethylenically unsaturated monomer containing acid groups such as carboxylic acid groups, sulfonic acid groups or acidic sulfate ester or phosphate ester groups, and (c) a crosslinking agent, such as a glycol diacrylate or dimethacrylate or divinyl benzene, etc.; and also, preferably, (d) at least one acrylic monomer capable of polymerizing to a very high molecular weight; there may also be present (e) other polymerizable ethylenically unsaturated monomers, which are copolymerizable with components (a), (b), (c) and (d).

BACKGROUND OF THE INVENTION

In my U.S. Pat. No. 3,532,679, issued Oct. 6, 1970, and entitled Hydrogels from Cross-linked Polymers of N-Vinyl Lactams and Alkyl Acrylates, I have described certain neutral hydrogels obtained by simultaneous polymerization and cross-linking of a mixture of an N-vinyl lactam, and alkyl acrylates. In my copending application Ser. No. 385,275 filed July 27, 1973, now U.S. Pat. No. 3,878,175 issued Apr. 15, 1975, I have described an improvement on my said patent, wherein a solution of the monomers in a hydrophobic solvent is simultaneously polymerized and cross-linked; whereby a highly absorbent, spongy, polymeric, neutral hydrogel is obtained.

I have now found that such N-vinyl lactam or other heterocyclic N-vinyl monomer based hydrogels can be modified, by incorporating an anionic monomer in the mixture of monomers being simultaneously polymerized and cross-linked, so that a hydrogel having anionic functionality, and thus new and useful properties, is obtained.

A number of synthetic polymeric materials, which contain acidic groups which impart anionic functionality thereto are known in the art; possibly the most widely available and best known of such anionic synthetic resins, are the cation exchange resins available under such trade-names as Amberlite, Dowex, Permutit and Zeocarb. In genereal the so-called "weak" cation exchange resins contain carboxylic groups while the so-called "strong" cation exchange resins contain sulfonic groups. However, such cation exchange resins are not hydrogels.

As disclosed in my prior U.S. Pat. No. 3,532,679, supra, various cross-linked hydrogels are known in the art. However, practically all of these known hydrogels are neutral hydrogels and are not inoic in character. While in U.S. Pat. No. 3,689,634, issued Sept. 5, 1972 to Kliment, Vacik, Majkus and Wichterle, entitled Protracted Activity Oral Hydrogel Bead; there is a broad suggestion that "it is also possible to replace the non-ionizable cross-linked hydrogels by physically similar hydrogels containing also ionizable groups"; the only examples of ionic hydrogels disclosed in this patent are: "A porous hydrogel capable of exchanging cations prepared by copolymerizing a mixture of 35 parts of methacrylic acid, and 30 parts of a 25 percent aqueous solution of maleic anhydride," disclosed in Example 8 at the top of column 8 of the patent; and "A copolymer prepared from 97 parts of ethylene glycol monomethacrylate, 2 parts of methacrylic acid and 1 percent of ethylene glycol bis-methacrylate by suspension polymerization in a concentrated, aqueous solution of sodium chloride, using 0.05 parts of diisopropyl percarbonate as a polymerization initiator," disclosed in Example 9 at the middle of column 8 of the patent. These prior art ionic hydrogels are obviously substantially different from those of the present invention; inter alia, the prior art hydrogels contain no N-vinyl lactam, or other N-vinyl heterocyclic monomer units and thus are structurally different from those of the present invention, and would be lacking in properties attributable to such N-vinyl lactam etc. units.

Other ionic synthetic polymeric materials which are known in the prior art, are the self-stabilizing polymer latices obtained by emulsion polymerization techniques in which a copolymerizable surfactant is used as an emulsifier in the preparation of the aqueous emulsion of monomer(s) to be polymerized. In the course of the polymerization, these copolymerizable surfactants copolymerized with the monomer or mixture of other monomers being polymerized and become an integral part of the resulting polymer so that the polymeric material so obtained contains ionic (acidic) groups. As examples of acidic, ionic, copolymerizable surfactants which have been so used may be mentioned the polymerizable α-methylene carboxylic acid esters (e.g., the acrylic and methacrylic acid esters) of hydroxyalkane sulfonic acids such as those disclosed in U.S. Pat. No. 3,024,211 and 3,033,833 both to Le Fevre and Sheetz and U.S. Pat. No. 3,617,368 to Gibbs and Wessling; also the sulfate esters of hydroxyalkyl acrylates and methacrylates disclosed in my U.S. Pat. No. 3,839,393 issued Oct. 1, 1974; also the phosphate esters of hydroxyalkyl acrylates and methacrylates disclosed in my copending application Ser. No. 321,229, filed Jan. 5, 1973, now U.S. Pat. No. 3,855,364; and the sulfates of polymerizable ethylenically unsaturated alcohols and their alkylene oxide adducts disclosed in my application Ser. No. 321,228, filed Jan. 5, 1973, now U.S. Pat. No. 3,875,202. Such copolymerizable surfactants are also used to impart hydrophilic properties to the resulting polymer, to improve the receptivity of the resulting polymer to basic dyes and other purposes more fully described in the above patents; however, none of the polymers heretofore produced by their use have, to the best of my knowledge, been in the form of hydrogels.

One of the outstanding advantages of the hydrogels of the present invention which contain anionic groups, as compared with the non-hydrogel form of anionic polymeric materials heretofore obtained by the use of anionic copolymerizable monomers, such as those mentioned above which contain carboxylic, sulfonic or sulfate groups, is that the hydrogel form of the anionic polymers of the present invention permits and assures much more intimate contact between the anionic groups of the anionic polymeric hydrogel and any basic material which it is desired to combine or complex therewith. In the presence of water the anionic hydrogels of the present invention are quite permeable and swollen. Due to this swelling the water, and any basic material dissolved or dispersed therein, of an aqueous medium with which these anionic hydrogels are used, or come in contact with during use, can readily diffuse or be transported throughout the hydrogel. As a result, combination or complexing of basic materials with the anionic groups of the polymeric hydrogel can and does take place throughout the hydrogel in contrast for example, with the essentially surface action in the case of cation exchange resins. This swelling also increases the distance between the anionic groups of the hydrogel and this is also conductive to more complete reaction. Thus basic materials can be combined or complexed much more efficiently and completely with the anionic groups of the anionic polymeric hydrogels of the present invention; and, conversely, basic materials which are complexed or otherwise combined with the anionic groups of the anionic polymeric hydrogels of this invention may be more efficiently released therefrom and transferred to an aqueous medium with which they are used; especially in comparison with corresponding ion exchange resins.

OBJECTS OF THE INVENTION

It is, therefore, an object of the present invention to provide a new class anionic polymeric materials, containing acidic groups, in the form of hydrogels having new and useful properties.

It is a further object of this invention to provide methods of making this new class of anionic hydrogels.

It is a further object of this invention to provide new and useful compositions and processes containing and/or utilizing the novel anionic hydrogels of this invention.

Other and further objects will be apparent as the present description progresses.

DETAILED DESCRIPTION OF THE INVENTION

As previously stated, the novel anionic hydrogels of this invention are obtained by simultaneous catalytic polymerization and cross-linking of a mixture of:
a. a heterocyclic N-vinyl monomer;
b. an ethylenically unsaturated monomer, which is copolymerizable with component (a) and which contains an acid group in its molecular structure; and
c. a cross-linking agent;

I also prefer to include in the monomer mixture:
d. at least one acrylic monomer capable of polymerizing to a very high molecular weight;

there may be present in the monomer mixture:
e. other polymerizable mono-ethylenically unsaturated monomers, which are copolymerizable with components (a), (b), (c) and (d).

Component (a)

The heterocyclic N-vinyl monomer, used as component (a) above, may be N-vinyl imidazole, having the formula:

Formula 1.

but I prefer to employ a heterocyclic N-vinyl monomer containing a carbonyl function adjacent to the nitrogen in its heerocyclic moiety and represented by the following formula:

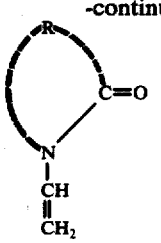

Formula 2.

wherein R represents a divalent aliphatic group, preferably alkylene, containing a linear chain of 3 to 5 atoms necessary to make up the 5 to 7 membered heterocyclic ring.

I particularly prefer N-vinyl-2-pyrrolidone or other N-vinyl lactams such as N-vinyl-2-piperidone or N-vinyl-E-caprolactam. These N-vinyl lactams may be substituted in the lactam ring by one or more lower alkyl groups such as methyl, ethyl or propyl. As examples of other heterocyclic N-vinyl-monomers, which may be used as component (a), either alone or in admixture with each other or in admixture with one or more N-vinyl lactams, may be mentioned: N-vinyl succinimide, N-vinyl diglycoylimide, N-vinyl glutarimide, N-vinyl-3-morpholinone, N-vinyl-5-methyl-3-mopr-holinone, N-vinyl imidazole, etc.

Component (b)

As component (b) — an ethylenically unsaturated monomer, which is copolymerizable with component (a) and which contains an acid group in its molecular structure — I may use any of the usual polymerizable or copolymerizable ethylenically unsaturated acids commonly used in vinyl and related polymerizations to produce polymers having acid functionality. These include such ethylenically unsaturated carboxylic acids as: acrylic acid, methacrylic acid, maleic acid, maleic anhydride, fumaric acid, itaconic acid, ethyl acid maleate, citraconic acid, crotonic acid, aconitic acid, cinnamic acid, and similar unsaturated carboxylic acids. However, I particularly prefer to employ as component (b) an ethylenically unsaturated polymerizable monomer in which the acid group is a sulfonic acid group, a sulfate ester group or a phosphate ester group. Such acidic monomers are employed in the form of the free acid or of their salts, e.g. as their ammonium or alkali metal, e.g. sodium or potassium, salts.

As examples of suitable polymerizable monomers which contain sulfonic acid groups may be mentioned; vinyl sulfonic acid, styrene sulfonic acid (e.g. p-vinylbenzenesulfonic acid), acrylamidoaryl sulfonic acids and acrylamidoalkyl sulfonic acids of the formula:

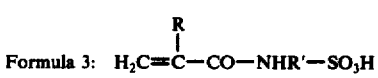

Formula 3: $H_2C=C-CO-NHR'-SO_3H$ wherein:
R is hydrogen or alkyl of 1 to 4 carbon atoms, and R' is an aryl or alkyl group having at least 2 carbon atoms separating N from S.

A number of specific polymerizable acrylamido aryl sulfonic acids and acrylamidoalkyl sulfonic acids of this type are disclosed in U.S. Pat. No. 2,983,712 issued May 9, 1961 to Wilkinson; I particularly prefer the acrylamidoalkyl sulfonic acids disclosed in said patent and also U.S. Pat. Nos. 3,332,904 issued July 25, 1967 to LaCombe and Miller; 3,478,091 issued Nov. 11, 1969 to Murfia and Miller; and 3,506,707 issued Apr. 14, 1970 to Miller and Murfia, such as 2-acrylamido-2-methylpropane-1-sulfonic acid.

Another preferred class of monomers containing sulfonic acid groups are the so-called copolymerizable surfactants which are esters of polymerizable α-methylene carboxylic acids, especially acrylic or methacrylic acid, with hydroxyalkane sulfonic acids, especially isethionic acids, and which may be represented by the formula:

Formula 4:
$$CH_2=\overset{R}{\underset{|}{C}}-COO-Q-SO_3-M$$

wherein, R is hydrogen, halogen (e.g., chlorine or bromine, or an organic radical, preferably alkylene of from 1 to about 6 carbon atoms; Q is a bivalent organic radical having its valence bonds on two different carbon atoms, preferably alkylene of from 2 to about 6 carbon atoms; and M is a cation, e.g., ammonium, amino, alkali metal or alkaline earth metal etc. A number of such esters, of α-methylene carboxylic acids with hydroxyalkane sulfonic acids, which may be used as component (b) are disclosed in U.S. Pat. No. 3,024,221 issued Mar. 6, 1962 to Le Fevre and Sheetz; and as examples thereof may be mentioned 2-sulfoethyl acrylate, 2-sulfoethyl methacrylate, 2-sulfoethyl(-α-ethylacrylate, 2-sulfoethyl-α-propylacrylate, 2-sulfoethyl-α-butylacrylate, 2-sulfoethyl-α-cyclohexylacrylate, 2-sulfoethyl-α-chloroacrylate, 3-sulfo-1-propyl methacrylate, 3-sulfo-1-propyl methacrylate, 3-sulfo-1-butyl acrylate, 4-sulfo-1-butyl acrylate, 4-sulfo-1-butyl methacrylate, ar-sulfophenyl acrylate, ar-sulfophenyl methacrylate, and other like esters disclosed in said U.S. Pat. No. 3,024,221. Also, the glycidyl acrylate sulfonate and glycidyl methacrylate sulfonate disclosed in U.S. Pat. No. 3,541,059 issued Nov. 17, 1970 to Shaper and in Japanese Pat. No. 73 32,089 issued Oct. 4, 1973 to Nippon Oils and Fats Co., Ltd.

As copolymerizable surfactants in which the acid group is a sulfate or phosphate group I particularly prefer the sulfate esters of hydroxyalkyl acrylates or methacrylates (or the hydroxyalkyl esters of similar α-methylene carboxylic acids) disclosed in my U.S. Pat. No. 3,839,393 issued Oct. 1, 1974; the sulfate esters of polymerizable ethylenically unsaturated alcohols and their alkylene oxide adducts disclosed in my prior application Ser. No. 321,228 filed Jan. 5, 1973; and the phosphate esters of hydroxyalkyl acrylates and methacrylates disclosed in my prior U.S. Pat. No. 3,855,364 issued Dec. 17, 1974. These types of sulfate or phosphate ester monomers may be represented, respectively, by the following general formulas:

Formula 5:
$$CH_2=\overset{R}{\underset{|}{C}}-COO-(CH_2-\overset{R'}{\underset{|}{CH}}-O-)_n-SO_3M$$

Formula 6:
$$\overset{R''}{\underset{|}{CH}}=\overset{R}{\underset{|}{C}}(CH_2)_m-O-(CH_2-CH-O-)_n-SO_3M \text{ and}$$

-continued

Formula 7:
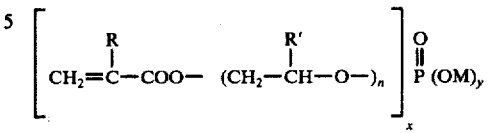

In the forgoing formulas 5, 6 and 7:
R represents hydrogen or alkyl of 1 to about 6 carbons;
R'' represents hydrogen, methyl or phenyl;
R' represents hydrogen, or alkyl, preferably methyl or ethyl
m represents an integer of from 1 to about 18;
n represents an integer, preferably of from 1 to about 4;
x represents an integer of from 1 to 2;
y represents an integer of from 1 to 2, provided that the sum of x and y is 2; and
M represents a cation, i.e. hydrogen, ammonium, amino, alkali metal or alkaline earth metal.

As examples of specific materials of these types may be mentioned; 2-sulfatoethyl acrylate, 2-sulfatoethyl methacrylate, 2-sulfatopropyl acrylate, 2-sulfatopropyl methacrylate, 2-sulfatobutyl acrylate, 2-sulfatobutyl methacrylate, ω-sulfatodiethyleneglycol monoacrylate, ω-sulfatodiethylenglycol monomethacrylate, ω-sulfato-triethyleneglycol monoacrylate, ω-sulfato-triethyleneglycol monomethacrylate and other analogous materials disclosed in said U.S. Pat. No. 3,839,393.

Also the sulfates of such monoethylenically unsaturated alcohols as allyl alcohol, allyl carbinol, methallyl alcohol, hexen-1ol-6, octen-1-ol-8, undecenyl alcohol (undecen-1-ol-11), dodecen-1-ol-12, tetradecen-1-ol-14, cinnamyl alcohol and the like, and the sulfates of alkylene oxide adducts (ethylene oxide, propylene oxide or butylene oxide adducts) of the forgoing unsaturated alcohols, such as 2-hydroxyethyl ether of allyl alcohol, 2-hydroxyethyl ether of butene-1-ol-4,2-hydroxyethyl ether of undecenyl alcohol, the monoallyl ethers of di-, tri- and tetra-ethylene glycol, the monohexenyl ethers of di-, tri-, and tetra-ethylene glycol, the mono-undecenyl ethers of di-, tri-, and tetraethylene glycol, the adduct of allyl alcohol with 3 molar proportions of ethylene oxide, the adduct of cinnamyl alcohol with 3 molar proportions of propylene oxide, the adduct of cinnamyl alcohol with a mixture of three molar proportions of ethylene oxide and two molar proportions of propylene oxide, the adducts of undecenyl alcohol with 12, 20, 35 and 50 molar proportions of ethylene oxide, the adduct of allyl alcohol with six molar proportions of 1,2-butylene oxide and 12 molar proportions of ethylene oxide and analogous materials disclosed in said application Ser. No. 321,228, now U.S. Pat. No. 3,875,202.

As examples of ethylenically unsaturated monomers containing phosphate ester groups may be mentioned the phosphate monoesters and phosphate di-esters of hydroxyalkyl acrylates and methacrylates, especially the mixtures of a major amount of the phosphate monoester and a minor amount of the phosphate diester of such hydroxyalkyl acrylates and methacrylates; as specific examples thereof may be mentioned the mixtures of about 55% to about 75% of the phosphates monosters of mono-, di- and/or tri-ethylene glycol monoacrylates and monomethacrylates with about 10% to about 20% of the phosphate diesters of the mono-, di-, and tri-ethylene glycol monoacrylates and monoethacrylates, and analogous materials of Formula 6 above, disclosed in my application Ser. No. 321,229, now U.S. Pat. No. 3,855,364 issued Dec. 17, 1974, and analogous unsaturated monomers containing phosphate ester groups.

Component (c)

As the cross-linking agent, component (c), I particularly prefer the alkylene glycol diacrylates or dimethacrylates and the polyalkylene glycol diacrylates and dimethacrylates, represented by the formula:

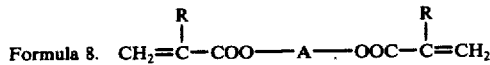

wherein,
R represents hydrogen or alkyl of 1 to 4 carbon atoms, and
A represents alkylene of from 2 to about 10 carbons or a polyglycol ether group of the formula

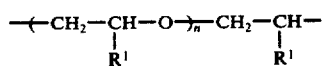

in which
$R^1$ represents hydrogen, methyl or ethyl, and
n is an integer of from 1 to about 20.

As examples thereof may be mentioned: ethylene glycol diacrylate, ethylene glycol dimethacrylate, propylene glycol diacrylate, propylene glycol dimethacrylate, diethylene glycol diacrylate, diethyleneglycol dimethacrylate, triethylene glycol diacrylate, triethylene glycol dimethacrylate, tetraethylene glycol diacrylate, tetraethylene glycol dimethacrylate, pentaethylene glycol diacrylate, pentaethylene glycol dimethacrylate, hexamethylene glycol diacrylate, hexamethylene glycol dimethacrylate, and mixtures of the foregoing. There may also be used such cross-linking agents as divinylbenzene, divinyl ether, divinyl toluene, diallyl tartrate, diallyl maleate, divinyl tartrate, N,N'-methylene-bis-acrylamide, and the like.

While I have obtained valuable anionic hydrogels by the use of a mixture of only monomer components (a), (b) and (c); I have found that the anionic hydrogels so produced may contain an appreciable amount of relatively low molecular weight polymers (i.e. polymers of a molecular weight of from 10,000 to 50,000) and may be somewhat less physically strong than desired, possibly due to the water solubility of their low molecular weight polymer content. While anionic hydrogels containing such relatively low molecular weight polymers may be preferred for certain applications, I have found that for most applications polymeric materials which are relatively free of such low molecular weight polymers are to be preferred. In order to assure the production of anionic hydrogels having the most desirable properties for most applications, I preferably include in the mixture of monomers, which is simultaneously polymerized and cross-linked, as component (d) of such mixture, an appreciable amount of at least one acrylic monomer capable of polymerizing to a very high molecular weight (100,000 or higher). The presence of such a component (d) serves to substantially increase the average molecular weight of the resulting anionic polymeric hydrogel and to minimize or eliminate the amount of relatively low molecular weight anionic polymers present therein.

Component (d)

Component (d) — an acrylic monomer capable of polymerizing to a very high molecular weight — is any acrylic monomer which may be represented by the following general formula:

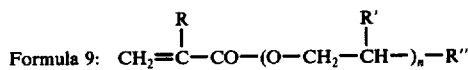

wherein:
R and R' each represent hydrogen, or lower alkyl of 1 to about 4 carbon atoms; and
R" represents hydroxyl, alkoxy or hydroxyalkoxy or, when n is 0 (zero), R" may also represent —NH$_2$ or

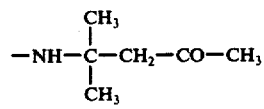

and n represents an integer (including 0) of from 0 to about 20.

As component (d), I particularly prefer acrylamides such as acrylamide, N-(1,1-dimethyl-3-oxobutyl) acrylamide also called diacetone acrylamide (described in U.S. Pat. No. 3,497,467, issued Feb. 24, 1970 to Coleman) and methacrylamide; hydroxyalkyl acrylates and methacrylates such as glyceryl monoacrylate and glyceryl monomethacrylate; and glycol monoacrylates and glycol monomethacrylates or monohydroxy (and monoalkoxy) polyalkylene glycol acrylates and methacrylates. Such hydroxy alkyl acrylates and methacrylates may be considered as the alkylene oxide adducts of acrylic or methacrylic acid with alkylene oxides, as they are generally produced by the reaction of one molar proportion of acrylic or methacrylic acid with one or several molar proportions of a lower alkylene oxide, such as ethylene oxide, propylene oxide or 1,2-butylene oxide. As examples of specific hydroxy alkyl acrylates and methacrylates and of monohydroxy (and monoalkoxy) polyalkylene glycol monoacrylates and monomethacrylates of Formula 9, which may be used as component (d), may be mentioned: hydroxyethyl acrylate, hydroxyethyl methacrylate, diethylene glycol monoacrylate, diethylene glycol monomethacrylate, triethylene glycol monoacrylate, triethylene glycol monomethacrylate, methoxyethylene glycol acrylate or methacrylate, methoxy polyethylene glycol acrylate or methacrylate, ethoxy ethylene glycol acrylate or methacrylate, ethoxy polyethylene glycol acrylate or methacrylate, butoxy ethylene glycol acrylate or methacrylate, 2-hydroxy propyl acrylate or methacrylate, 2-hydroxy butyl acrylate or methacrylate, polypropylene glycol acrylate or methacrylate, polybutyleneglycol acrylate and methacrylate and analogous hydroxyalkyl acrylates or methacrylates and monohydroxy (and monoalkoxy) polyalkylene glycol acrylates and methacrylates.

Such acrylic monomers as acrylonitrile, methacrylonitrile and alkyl acrylates amd methacrylates are also quite effective for increasing the molecular weight of the polymeric hydrogels of the present invention and may be used as component (d) if desired. It is quite possible and entirely feasible to use a mixture of several acrylic monomers as component (d) and from a cost standpoint it is frequently advantageous to use a mixture of say acrylamide with one or more of, the somewhat more expensive, hydroxyalkyl acrylates or methacrylates. The alkyl acrylates and methacrylates, especially the lower alkyl acrylates and methacrylates, are also less expensive than the hydroxyalkyl acrylates and methacrylates; so that, where cost is a controlling factor, it is often advantageous to replace all or part of the preferred hydroxyalkyl acrylates or methacrylates listed above with an alkyl acrylate or methacrylate. As examples of specific alkyl acrylates and methacrylates, which may be used as component (d), either alone or in admixture with each other or in admixture with one or more of the preferred hydroxyalkyl acrylates or methacrylates, listed above, may be mentioned: methyl acrylate, methyl methacrylate, ethyl acrylate, ethyl methacrylate, butyl acrylate, butyl methacrylate, hexyl acrylate, hexyl methacrylate, lauryl acrylate, lauryl methacrylate, etc. The lower members of this series are preferred, because of greater reactivity and because larger percentages can be incorporated into the copolymer without substantially reducing the percent swelling and hydrophilic characteristics of the copolymers.

Component (e)

As previously mentioned, if desired there may also be used, as component (e), other monoethylenically unsaturated monomers which are copolymerizable with components (a), (b), (c) and (d) in the mixture of monomers subjected tp simultaneous polymerization and cross-linking. As examples of specific monomers which may be used as component (e) may be mentioned: vinyl acetate, vinyl propionate, vinyl butyrate, vinyl chloride, vinylidene chloride, vinyl methyl ketone, styrene, methoxystryrene, monochlorostyrene, ar-methylstyrene, ar-ethylstyrene, a, ar-dimethylstyrene, ar, ar-dimethylstyrene, vinylnaphthalene, vinyl benzoate, ethyl vinyl ether, n-butyl vinyl ether, isobutyl vinyl ether and the like.

The fact that the anionic polymers of the present invention are hydrogels, as distinguished from a solid resinous structure, I attribute primarily to the amount of component (a) — the heterocyclic N-vinyl monomer component — used in their preparation or, when a component (d) is used and is a water-soluble acrylic monomer such as a hydroxyalkyl acrylate or methacrylate or a monohydroxy polyglycol monoacrylate or monomethacrylate, to the combined amount of component (a) and such component (d) used in their preparation; and only secondarily to the amount of cross-linking agent, component (c), which is used. Within the proportions, specified below, of monomer components, the amount of cross-linking agent appears to effect primarily the degree of water swellability of the hydrogel. With any given recipe the swellability (expressed as water content at equlibrium at 25° C., in percent by weight), of the hydrogel ultimately obtained, decreases as the amount of cross-linking agent employed therein is increased; and is thus inversely proportional to the amount of crosslinker used.

The anionic character of the ionic hydrogels of the present invention is attributable to the amount of component (b) — the monoethylenically unsaturated monomer containing an acid group — used in their preparation; and the amount of cationic materials which may be combined or complexed with them is directly proportional to the amount of component (b) used. Thus the particular application contemplated for the anionic hydrogel and the amount of cationic material, with which it is desirable that they be able to combine, will primarily determine the amount of component (b) to be used.

Considerable variation is possible in the relative amount of each of the forgoing monomer components (a), (b), (c), (d) and (e) which is used and an anionic polymeric hydrogel is obtained when the mixture of such monomer components which is subjected to simultaneous polymerization and cross-linking is composed of:

| % by weight (based on total weight of all monomer components used) | Component |
|---|---|
| about 20% to about 95% | (a)- the heterocyclic N-vinyl monomer. |
| about 50% to about 0.05% | (b)- the monethylenically unsaturated monomer which contains an acid group in its molecular structure. |
| about 0.2% to about 12% | (c)- the cross-linking agent. |
| 0% to about 50% | (d)- the acrylic monomer capable of polymerizing to a very high molecular weight. |
| 0% to about 30% | (e)- a.polymerizable monoethylenically unsaturated monomer. |

It will be understood that while the primary function served by component (d), when it is used, is to increase the molecular weight of the anionic hydrogel which is ultimately obtained and to minimize or eliminate the presence of relatively low molecular polymers in the ultimate hydrogel; component (d) can also be considered as an extender or partial replacement of the heterocyclic N-vinyl monomer, component (a). When a component (d) is used, the total amount of component (d) which is used in any particular recipe should not exceed the amount of component (a) used in the same recipe. However the total amount of both component (a) and component (d) which is used should not exceed the maximum amount of component (a) (95% by weight of the total monomers) specified above. This can also be expressed "(a)$\geq$(d) and (a) + (d) = about 40% to about 95% by weight of the total weight of all monomers used".

Polymerization and Cross-Linking

The simultaneous polymerization and cross-linking to make the hydrogels of the present invention may be carried out by various techniques known in the art. Thus the polymerization and cross-linking may be effected by bulk polymerization of a mixture of the several monomer components (a), (b), (c), and (d) and (e) if desired, in the proportions given above, in the presence of a free radical polymerization catalyst such as any of the well known inorganic or organic peroxides, azobisisobutyronitrile, etc. polymerization catalysts.

Such catalysts may be employed in the range of about 0.05 to about 4% of the total monomers. The preferred amount of catalyst is about 0.1 to about 2.0% of the monomer components. Typical catalysts include MEK peroxide (methyl ethyl ketone peroxide), lauroyl peroxide, t-butyl-peroctoate, benzoyl peroxide, isopropyl percarbonate, cumene hydroperoxide, dicumyl peroxide, azobisiso-butyronitrile, potassium persulfate, potassium peroxide, etc. Irradiation, as by ultraviolet light or gamma rays, also can be used to catalyze the polymerization and cross-linking.

The polymerization and cross-linking may be effected at temperatures in the range of 20° C. to 100° C. or somewhat higher, preferably in the range of 35° C. to about 60° C., until most of the polymerization is effected, followed by a post-cure at about 100° C to about 125° C. for about an hour.

Advantageously, the polymerization and cross-linking may be effected by the use of a casting technique of the type described in my said U.S. Pat. No. 3,532,679 in which a mixture of the monomer components, catalyst and, if desired, a mold release agent is deaerated, as by the application of vacuum until air bubbles no longer rise to the surface, poured into a suitable mold, such as a polymerization tray or cell, which is then sealed and held at a suitable temperature, as by placing in a circulating air oven or heating bath, until a hard polymer is obtained. The hard polymer so obtained may be further cured by heating to a somewhat higher temperature, than that used for the polymerization, such as 100° C to 125° C for about an hour. The cell is then opened and the cured polymer removed therefrom. The mold may be in the shape of the desired product or the solid polymer may be fabricated, after curing, into the desired shape; e.g., it may be ground into a powder or cut into the desired shape. Such polymerization and cross-linking may also be carried out in the manner described in my copending application Ser. No. 385,275, filed July 27, 1973, now U.S. Pat. No. 3,878,175 issued Apr. 15, 1975, wherein a solution of the several monomer components in an inert, nonpolar hydrophobic liquid such as silicone liquid, hexane, octane, mineral oil, toluene, xylene, etc. is simultaneously polymerized and cross-linked; whereby the polymer can ultimately be obtained in a porous or spongy or foamy form.

It will also be understood that the simultaneous polymerization and cross-liking may be effected, employing solvent polymerization techniques, in the presence of water-soluble solvents in which the monomer components (a), (b), (c), (d) and (e) are soluble. Such solvents include the lower aliphatic alcohols such as methanol, ethanol, propanol and isopropanol; acetone, dioxane, ethylene glycol, glycol esters or ethers etc. By such procedures the polymer is obtained in the form of an organogel from which the organic solvent may be removed by washing with water or by distillation or evaporation.

The polymer so obtained by casting may then be immersed in water and thereby gradually swollen into a hydrogel. In the case of polymers produced in a casting technique involving the use of either a hydrophobic or water soluble solvent and which thus still contain the solvent, the solvent is displaced by the water during the immersion. Such displacement of the solvent by the water may be speeded up by kneading or squeezing the polymer during the swelling, as by passing it between squeeze rollers. The swelling in water is continued until equilibrium is reached, or until a hydrogel containing the desired amounts of water is reached. The anionic hydrogels so obtained are soft pliable materials which can be reacted with cationic materials.

It will be appreciated that polymeric products having a predetermined shape may be obtained by the use of molds of the desired shape. Thus, a product having a definite curved shape may be obtained by casting between a pair of curved glass sheets. Rods may be obtained by casting and curing in glass or plastic (e.g. nylon or polyethylene) tubes. Hollow tubes can be cast between two concentrically disposed glass tubes or by centrifugal casting procedures under polymerization conditions.

Further details of the present invention are illustrated in the specific examples which follow of preferred embodiments thereof. In these examples the polymeric anionic hydrogels were prepared employing a conventional type casting cell prepared by inserting a soft and flexible, three-sixteenth inch thick, vinyl gasket between two pieces of 8 × 12 × ¼ inch polished plate glass, the gasket being positioned about one inch from the edge of the glass sheets. The glass plates were then clamped with spring type clamps, such as one inch binder clips or sprig loaded clamps. The size of the cell is not critical but will depend on the size of cast sheet desired and any size limitations of the oven or heating bath to be employed. For laboratory preparations I have found glass sizes of up to 16 × 16 inches to be convenient. The thickness of the gasket should be about 20–30% greater than the desired thickness of the final cast sheet and round, square or rectangular gaskets with sides or diameter of from about 0.8 inch to about 0.5 inch may be used to control sheet thickness. Rods may conveniently be cast in sealed glass, nylon, polyethylene, etc. tubing of approximately ¼ inch diameter and 12 – 18 inches long.

The casting mixture consisting of monomers, catalyst, mold release agent or other additives if desired, was deaerated by application of vacuum until air bubbles no longer rose to the surface. The deaerated casting mixture is then poured into the casting cell which is then sealed and placed horizontally on a shelf in a circulating air oven equipped with constant temperature control. Unless otherwise specified it was kept in this oven at 50°–55° C. until substantially polymerized, usually in 18–48 hours. The temperature is then raised gradually (over 2–4 hours) to approximately 100° C, and polymerization completed during 1 to 3 hours at 100°–125° C. The mold was allowed to cool to room temperature, the clips removed, and the mold pried open to release a clear, colorless and rigid sheet.

EXAMPLE 1.

To a 1 liter, three neck flask equipped with a mechanical stirrer and vacuum line there was charged the following reactants:

80 grams of N-vinyl-2-pyrrolidone,
20 grams of methacrylic acid
0.6 grams of tetraethylene glycol dimethacrylate and
2.0 grams of MEK provide*, 11.5% active oxygen.

*LUPERSOL DSW, containing 11.5% active oxygen, obtained from Lucidol Division of Pennwalt Corp.

The flask was thoroughly purged with nitrogen while stirring to effect solution and vacuum was then applied until gas bubbles no longer rose to the surface. The solution in the flask was then poured into a laboratory size glass casting cell consisting of two pieces of 8 × 12 inches plate glass, ¼ inch thick, clamped to three-sixteenth inch thick soft vinyl gasket. The sealed mold was laid on the shelf in a circulating air oven equipped with constant temperature control and maintained at 60° C. for 40 hours. Polymerization and cross-linking was then continued by gradually raising the temperature of the oven to 100° C. over a three hour period and holding at this temperature for one hour. The mold was removed from the oven and allowed to cool to room temperature, the clamps removed and the mold then pried open.

The thus obtained clear, rigid, hard sheet was then immersed in water and allowed to swell until equilibrium had been reached. The thus obtained hydrogel was a tough pliable material, the water content of which, at equilibrium at 25° C., was 24.6% by weight.

fied in proportions within the ranges specified. Additional specific recipes useful for the production of anionic hydrogels by the process of Example 1 or analogous procedures are given immediately below in tabular form.

Table 1.

| COMPONENT Recipe | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| (a) N-vinyl pyrrolidene | 65 | 40 | 55 | 50 | 25 | 30 | 50 | 90 | 70 | 65 | 50 | 50 | | | 55 | 50 |
| N-vinyl piperidone | | | | | | | | | | | | | 55 | 50 | | |
| Beta sulfoethyl methacrylate | 5 | 25 | | | | | | | | | | | | | | |
| NH$_4$-salt of 2-hydroxyethyl methacrylate sulfate | | | 10 | 30 | 50 | | | | | | | | 10 | | 10 | |
| Glycidyl methacrylate sulfonate | | | | | | | | 5 | 20 | | | | | | | |
| Sodium salt of 2-methacrylamido-2-methylpropane-1-sulfonic acid | | | | | | | | | | 5 | 10 | | | | | |
| (b) 2-hydroxyethyl methacrylate phosphate | | | | | | | | | | | | | 10 | | 10 | 10 |
| Methacrylic acid | | | | | | 10 | | | | | | | | | | |
| Acrylic acid | | | | | | | 20 | | | | | | | | | |
| (c) Triethylene glycol dimethacrylate | .8 | | | | | | | | .4 | | | | | | | |
| Polyethylene glycol (400) dimethacrylate | | .5 | .4 | .4 | .4 | .3 | .35 | .8 | .9 | .6 | .25 | .15 | .4 | .3 | .4 | .7 |
| Acrylamide | | 15 | | | | | 15 | 5 | 10 | | | | | | | |
| Methacrylamide | 10 | | | | | | | | | | | | | | | |
| Hydroxyethyl methacrylate | 20 | 20 | 35 | 20 | 25 | 30 | | | | 20 | 40 | 40 | 35 | 40 | | 20 |
| (d) Hydroxyethyl acrylate | | | | | | | | | | | | | | | 35 | |
| Hydroxypropyl acetate | | | | | | | | | | | | | | | | 20 |
| Methyl acrylate | | | | | | | 15 | | | 10 | | | | | | |
| Methyl methacrylate | | | | | | 30 | | | | | | | | | | |
| Water | 20 | | | | | | | 15 | 50 | 20 | 40 | | | | | |
| Catalyst MEK peroxide, 11.5% active oxygen | | 1.4 | | | 1 | 1 | | | | | 1.5 | | 1 | | 1 | .9 |
| Isopropyl percarbonate | | .1 | .4 | .05 | | | | .2 | | | | | .4 | | | .1 |
| Potassium persulfate | .3 | | | | | | | | | | | .25 | | | | |
| Azo bis isobutyronitrile | | | | .6 | | | .25 | 2 | .8 | | | | | | | |

EXAMPLE 2.

The procedure of Example 1 was repeated using the following charge of reactants:

60.0 grams of N-vinyl pyrrolidone,
20.0 grams of acrylamide,
20.0 grams of methylmethacrylate,
1.0 grams of the sodium salt of the sulfate ester of 2-hydroxylethyl methacrylate,
0.6 grams of tetraethylene glycol dimethacrylate and
2.0 grams of MEK peroxide, 11.5% active oxygen.

The resilient pliable hydrogel ultimately obtained had a water content of 72% by weight at equilibrium at 25° C.

EXAMPLE 3.

The procedure of Example 1 was again repeated using the following charge of reactants:

60.0 grams of N-vinyl pyrrolidone,
20.0 grams of acrylamide,
20.0 grams of methyl acrylate,
1.0 grams of the ammonium salt of the sulfate ester of 2-hydroxyethylacrylate,
0.6 grams of tetraethylene glycol dimethacrylate and
2.0 grams of MEK peroxide, 11.5% active oxygen The soft pliable rubbery hydrogel ultimately obtained had a water content of 82% by weight at equilibrium at 25° C.

The hydrogels of Examples 2 and 3 were washed with acidified water, containing sufficient HCl to give a pH of 1.0, to convert the sulfate ester groups of the sulfate ester of 2-hydroxyethyl methacrylate units of the copolymer to their free acid form and then given a final wash with distilled water to remove any HCl remaining therein. Samples of the thus treated hydrogels of Examples 2 and 3 and also of the hydrogel of Example 1 readily react with basic materials when placed in aqueous solutions or dispersion of the basic material.

It will be understood that the forgoing examples are illustrative only of the present invention and are not to be interpreted as limiting the invention. A wide variety of anionic hydrogels can readily be produced employing other specific reactants of the type heretofor specified in proportions within the ranges specified.

The thus obtained anionic hydrogels of the present invention have a variety of applications in the arts. As previously stated they may readily be combined, by reaction or complexing, with materials having a basic (cationic) group or groups. Such combination with basic materials may be effected by immersing or swelling the anionic hydrogel in an aqueous solution or suspension of the basic material which it is desired to combine or complex therewith. Alternatively, if the basic material to be combined or complexed with the hydrogel is stable at the conditions used for polymerization and cross-linking, such basic material may be added to the mixture of monomers prior to or during polymerization and cross-linking so that the anionic hydrogel is obtained directly in the form of its desired reaction product or complex with such basic material. Alternately one can first form the salt or complex of component (b) — the ethylenically unsaturated monomer which contains an acid group in its molecular structure — with such stable basic (cationic) materials and use such salt or complex as component (b) in the simultaneous polymerization and cross-linking.

Thus the anionic hydrogels of the present invention, in the form of their alkali metal salts may be used as cation exchangers in a manner analogous to cation exchange resins. The anionic hydrogels of this invention are particularly valuable for combination with basic biologically active materials as basic agricultural chemicals, basic drugs and other pharmaceuticals, hormones, enzymes and basic cosmetic materials.

As examples of agricultural chemicals which may be combined with the anionic hydrogels of this invention and which are slowly released therefrom under conditions of use, when applied to plants, may be mentioned: such herbicides as Atrazine; 2,4-dichloro-6-(o-chloroanilino)-s-triazine; 2-(ethylamino)-4-isopropylamino)-6-(methylthio)-s-triazine; 2-chloro-4-ethylamino-6-isopropylamino-s-triazine; 2-t.butylamino-4-ethylamino-6-thio-s-triazine; 2-4-bis(3-methoxypropyl)-amino -6-methylthio-s-triazine; 2-4-bis- (isopropylamino)-6-methoxy-s-triazine; 2-4-bis(isopropylamino)-6-methylthio-s-triazine; and 2-chloro-4,6-bis(isopropylamino)-s-triazine.

As examples of basic pharmaceutical products which may be combined with the anionic hydrogels of this invention may be mentioned: Atropine; Atropine-N-oxide; dextroamphetamine; racemic amphetamine; ephedrine; d-desoxyephedrin; homatropine; imipramine; chlorophenoxamine; phenylephrine; phenmetrazine; phenazocine; procaine; strychnine; etc. Also such basic narcotics as codein and morphine; anticonvulsants as: diphenyl hydantoin; and pro-diphenyl hydantoin:

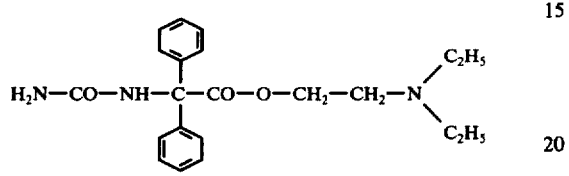

described in C&EN of September 22, 1974, page 26; basic antibiotics as: streptomycin; tetracycline; terramycine and aureomycine; basic hormones as insulin and thyroxin; basic vitamins as Vitamin K$_6$; basic tranquilizers as: promazine; chlorpromazine; dichlorpromazine; prochlorperazine; trifluoperazine; thiopropazate; chlorprothixene; and reserpine; basic antihistamines as: diphenylhydramine; pyrilamine; pheniramine; and chlorpheniramine; such glaucoma treating agents as: carbachol; epinephrine or its dipivalate ester known as pro-epinephrine (described in C&EN, September 22, 1974, page 26); and pilocarpine; also basic narcotic antagonists as: cyclazocine (2-cyclopropylmethyl-2'-hydroxy-5,9-dimethyl-6,7-benzomorphan or, using Chem. Abstracts nomenclature and numbering, 1,2,3,4,5,6-hexahydro-6,11-dimethyl-2,6-methano-3 benzazocin-8-ol) and other narcotic antagonists of the general formula (Chem. Abstracts numbering):

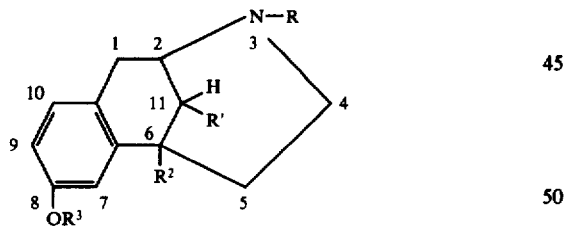

wherein:
R is a hydrocarbon radical about 4.4 A in length. e.g., propyl, butyl, cyclopropylmethyl or allyl;
R' and R$^2$ are lower alkyl groups (R' may be H) which may be joined to form a cyclohexane ring;
and R$^3$ is H, alkyl or acyl, i.e., the substituent in 8-position is a hydroxyl, ether or ester group;
described by S. Archer, N. F. Albertson and A. K. Pierson in a paper entitled "Structure-activity relationships in the opioid antagonists" appearing at pages 25–29 of Agonist Antagonist Actions Narcotic Analg. Drugs, Proc. Int. Symp. 1971, edited by H. W. Kosterlitz and published 1973 by Univ. Park Press, Baltimore, Md.; and by F. M. Robinson in Chapter 3. Analgesics and Narcotic Antagonists at pages 31–38 of Annu. Rep. Med. Chem. 1972.

I claim:
1. The anionic, polymeric hydrogel produced by simultaneous polymerization and cross-linking in the presence of a free radical polymerization catalyst in an amount of from about 0.05 to about 4 weight percent, based on the total weight of monomers, and at a temperature of from about 20° C. to about 125° C., of a mixture consisting essentially of the following monomers:
   a. about 20 to about 95 weight percent, based on the total weight of monomers, of a heterocyclic N-vinyl monomer selected from the group consisting of N-vinyl lactams, N-vinyl succinimide, N-vinyl diglycoylimide, N-vinyl glutarimide, N-vinyl-3-morpholinone, N-vinyl-5-methyl-3-morpholinone and N-vinyl imidazole;
   b. about 50 to 0.05 weight percent, based on the total weight of monomers, of a monoethylenically unsaturated anionic monomer, capable of copolymerizing with (a), and which contains in its molecular structure a sulfonic acid group and is selected from the group consisting of acrylamido aryl sulfonic acids, acrylamido alkyl sulfonic acids, glycidyl acrylate sulfonic acid, glycidyl methacrylate sulfonic acid, and esters of α-methylene carboxylic acids with hydroxysulfonic acids which esters have the formula: R'' — COO — Q — SO$_3$M, wherein
   R'' represents a member of the group consisting of vinyl and α substituted vinyl,
   Q represents a divalent hydrocarbon radical havig its valence bonds on different carbon atoms, and
   M is a cation;
   c. about 0.2 to about 12 weight percent, based on the total weight of monomers, of a polymerizable cross-linking agent, capable of copolymerizing with (a) and (b) and having the formula:

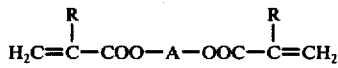

wherein
   R represents a member of the group consisting of hydrogen and alkyl of from about 1 to about 4 carbon atoms;
   A represents alkylene of from 2 to about 10 carbon atoms or a polyglycol ether group of the formula:

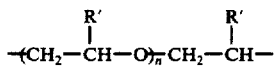

in which
   R' represents a member of the group consisting of hydrogen and alkyl of 1 to 2 carbon atoms, and
   n represents an integer of from 1 to about 20; and
   d. from 0 to about 50 weight percent, based on the total weight of monomers, of a monoethylenically unsaturated acrylic monomer capable of copolymerizing with (a), (b) and (c) and capable of polymerizing to a high molecular weight, in excess of 100,000, and selected from the group consisting of acrylamides, methacrylamides, acrylonitrile, methacrylonitrile, alkyl acrylates and methacrylates, and monohydroxy and monoalkoxy polyalkylene glycol acrylates and methacrylates; and
   provided that (a) ≧ (d) and (a) + (d) = about 40 to about 95 weight percent.

2. The anionic, polymeric hydrogel as defined in claim 1, wherein the N-vinyl monomer specified as (a) is an N-vinyl lactam.

3. The anionic, polymeric hydrogel as defined in claim 1, wherein the N-vinyl monomer specified as (a) is N-vinyl-2-pyrrolidone.

4. The anionic, polymeric hydrogel as defined in claim 2, wherein the acrylic monomer capable of polymerizing to a high molecular weight specified as (d) is an acrylic monomer having the formula:

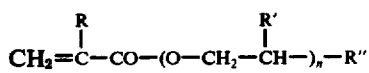

wherein:
R and R' each represents hydrogen or lower alkyl of 1 to about 4 carbon atoms;
R" represents hydroxyl, alkoxy or hydroxyalkoxy or, when $n$ is 0, R" may also represent —$NH_2$ or

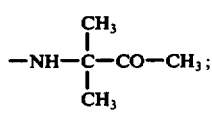

and N represents an integer (including 0) of from 0 to about 20.

5. The anionic, polymeric hydrogel as defined in claim 3, wherein the acrylic monomer capable of polymerizing to a very high molecular weight specified as (d) is an acrylic monomer having the formula:

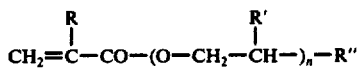

wherein:
R and R' each represents hydrogen or lower alkyl of 1 to about 4 carbon atoms;
R" represents hydroxyl, alkoxy or hydroxyalkoxy or, when $n$ is 0, R" may also represents —$NH_2$ or

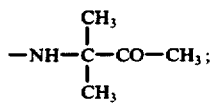

and $n$ represents an integer (including 0) of from 0 to about 20.

6. The anionic, polymeric hydrogel as defined in claim 1, wherein the polymerizable ethylenically unsaturated monomer containing an acid group specified as (b) is an ester of an α-methylene carboxylic acid with a hydroxysulfonic acid which ester has the formula:

wherein
R" represents a member of the group consisting vinyl and α substituted vinyl;
Q represents a divalent hydrocarbon radical having its valence bonds on different carbon atoms; and
M is a cation.

7. The anionic, polymeric hydrogel as defined in claim 6, wherein the N-vinyl monomer specified as (a) is an N-vinyl lactam.

8. The anionic, polymeric hydrogel as defined in claim 6, wherein the N-vinyl monomer specified as (a) is N-vinyl-2-pyrrolidone.

9. The anionic, polymeric hydrogel as defined in claim 7, wherein the acrylic monomer capable of polymerizing to a high molecular weight specified as (d) is an acrylic monomer having the formula:

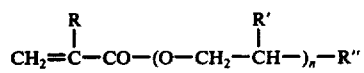

wherein:
R and R' each represent hydrogen or lower alkyl of 1 to about 4 carbon atoms;
R" represents hydroxyl, alkoxy or hydroxyalkoxy or, when $n$ is 0, R" may also represent —$NH_2$ or

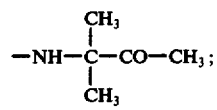

and $n$ represents an integer (including 0) of from 0 to about 20.

10. The anionic, polymeric hydrogel as defined in claim 8, wherein the acrylic monomer capable of polymerizing to a very high molecular weight specified as (3) is an acrylic monomer having the formula:

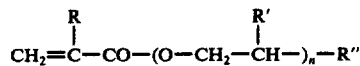

wherein:
R and R' each represents hydrogen or lower alkyl of 1 to about 4 carbon atoms;
R" represents hydroxyl, alkoxy or hydroxyalkoxy or, when $n$ is 0, R" may also represents —$NH_2$ or

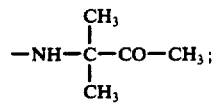

and $n$ represents an integer (including 0) of from 0 to about 20.

* * * * *